United States Patent [19]

Budge et al.

[11] Patent Number: 5,196,602
[45] Date of Patent: Mar. 23, 1993

[54] TWO-STAGE MALEIC ANHYDRIDE HYDROGENATION PROCESS FOR 1,4-BUTANEDIOL SYNTHESIS

[75] Inventors: John R. Budge, Cleveland Hts.; Thomas G. Attig, Aurora; Anne M. Graham, Northfield, all of Ohio

[73] Assignee: The Standard Oil Company, Cleveland, Ohio

[21] Appl. No.: 814,644

[22] Filed: Dec. 30, 1991

[51] Int. Cl.$^5$ .................. C07C 29/149; C07C 31/20
[52] U.S. Cl. .................... 568/864; 549/233; 549/325
[58] Field of Search ............................ 568/864

[56] References Cited

U.S. PATENT DOCUMENTS 4,010,197  3/1977  Toriya et al. .............. 568/864
4,301,077  11/1981 Pesa et al. ................. 568/864
5,073,650  12/1991 Stabel et al. ............... 568/864

Primary Examiner—Joseph E. Evans
Attorney, Agent, or Firm—D. P. Yusko; M. F. Esposito; L. W. Evans

[57] ABSTRACT

Maleic anhydride is hydrogenated to produce 1,4-butanediol in a two-stage process. In the first stage maleic anhydride and/or maleic acid contacted with hydrogen at a temperature of about 100° C. to about 350° C. in the presence of a suitable hydrogenation catalyst to produce succinic anhydride and/or gamma-butyrolactone. In the second stage, the succinic anhydride and/or gamma-butyrolactone and hydrogen are contacted at a temperature of about 180° C. to about 350° C. in the presence of a ruthenium-containing hydrogenation catalyst to produce 1,4-butanediol.

13 Claims, No Drawings

TWO-STAGE MALEIC ANHYDRIDE HYDROGENATION PROCESS FOR 1,4-BUTANEDIOL SYNTHESIS

FIELD OF THE INVENTION

This invention relates to a process for the manufacture of 1,4-butanediol. More specifically, the invention relates to the catalytic hydrogenation of maleic anhydride in the presence of ruthenium-containing hydrogenation catalysts to produce high yields of 1,4-butanediol.

DESCRIPTION OF THE PRIOR ART

Processes for manufacturing 1,4-butanediol from oxygenated $C_4$ hydrocarbons are well known. A recent example is U.S. Pat. No. 4,155,919 which teaches a single-stage process for converting maleic anhydride into 1,4-butanediol and/or tetrahydrofuran by contacting the maleic anhydride with hydrogen at specified conditions in the presence of a catalyst containing nickel, molybdenum and/or tungsten, and optionally zirconium and/or niobium. Reaction conditions include a temperature from 170°–215° C. and a pressure of from 125–200 bars. Other known processes are cited in that teaching over columns 1–4. Still other processes are known and include U.S. Pat. Nos. 3,113,138, 3,957,827 and 3,370,067. While all of these processes are useful for their intended purpose, all are subject to improvement. Two disadvantages common to many of these processes are the need to use high pressures; e.g., in excess of 1500 psi, and generally unsatisfactory product yield; i.e., they are not very product specific to the production of 1,4-butanediol.

U.S. Pat. No. 4,301,077 taught that with the use of ruthenium-containing catalysts, the pressure required to hydrogenate $C_4$ hydrocarbons to 1,4-butanediol and tetrahydrofuran could be effectively lowered to a range between 1000 to 1300 psi. However, this process also was not product specific to 1,4-butanediol and the life of the ruthenium-containing catalyst was not sufficiently long for commercial operations.

SUMMARY OF THE INVENTION

According to the process of this invention, 1,4-butanediol is manufactured from maleic anhydride by contacting maleic anhydride with hydrogen in a two-stage process wherein in the first stage, at least one of maleic anhydride or maleic acid is hydrogenated to succinic anhydride or succinic acid, gamma-butyrolactone or mixtures thereof at a temperature of 100° C. to about 350° C. in the presence of a hydrogenation catalyst and wherein in the second stage the succinic anhydride or succinic acid, gamma-butyrolactone or mixtures thereof is hydrogenated to 1,4-butanediol at a temperature of about 180° C. to about 350° C. in the presence of a hydrogenation catalyst of the formula $$Ru_{0.001-2}M_{0.01-2}M'_{0.01-2}M''_{0.01-1}O_x$$

where

M is at least one of nickel and palladium,

M' is at least one of iron, cobalt, rhodium, osmium, iridium and platinum,

M" is at least one of zinc and cadmium, and x is a number sufficient to satisfy the valency requirements of the other elements present.

wherein the total contact time for both stages combined is 0.1 minutes to 10 minutes at a pressure of about 750 psi to about 1500 psi.

DETAILED DESCRIPTION OF THE INVENTION

This invention is an improved process for the hydrogenation of maleic anhydride or maleic acid to 1,4-butanediol. The improvement involves carrying out an initial hydrogenation to convert the maleic anhydride to the more stable succinic anhydride, gamma-butyrolactone or mixtures thereof. The succinic anhydride and/or gamma-butyrolactone are then reacted in the presence of a ruthenium-containing hydrogenation catalyst to yield the 1,4-butanediol.

Reactants

Maleic anhydride,

HCH=CHC(O)OC(O), is derived from a number of sources. Most maleic anhydride is produced by passing a mixture of benzene or butane over a vanadium oxide catalyst at about 450° C. Maleic anhydride is also produced as a by-product from the manufacture of phthalic anhydride from naphthalene or by the catalytic oxidation of butylenes. Maleic acid, HOOCHC=CHCOOH, is derived from many of the same sources as maleic anhydride. Maleic acid may be used in place of or in addition to maleic anhydride which is the preferred feedstock for the instant process. For ease of description the remainder of the specification shall refer to maleic anhydride only.

Hydrogen is generally employed as a undiluted gas but it can be diluted with another gas if desired. If a diluent gas is used, it is typically an inert gas; i.e., a nonreactant with the process starting materials, catalyst and products at process conditions.

Catalyst

The hydrogenation of maleic anhydride to 1,4-butanediol is conducted in two stages. In the first stage, maleic anhydride is hydrogenated in the presence of a catalyst to succinic anhydride and/or gamma-butyrolactone. In the second stage, the first stage product (succinic anhydride and/or gamma-butyrolactone) is hydrogenated in the presence of a catalyst to 1,4-butanediol. The catalyst for the first stage may be any hydrogenation catalysts which will effect the conversion of maleic anhydride to succinic anhydride. Representative of suitable hydrogenation catalysts for this purpose are copper chromite, $Pd/Al_2O_3$, Pd on a carbon support, or mixed oxide catalysts comprising copper, zinc and aluminum. The hydrogenation catalyst for the second stage is a ruthenium-containing catalyst.

The ruthenium-containing catalyst used herein is of the formula $$Ru_{0.001-2}M_{0.01-2}M'_{0.01-2}M''_{0.01-1}O_x$$

where M, M', M" and x are as previously defined. Preferably, M is nickel, M' is iron, cobalt or rhodium and M" is zinc. Preferably, the molar ratio of ruthenium is between about 0.01 and 1.5, of M and M, between about 0.1 and 1.5, and of M" between 0.05 and 0.8. More preferably, the molar ratio ruthenium is between about 0.1 and 1.5, of M and M' between about 0.5 and 1.5, and of M" between about 0.1 and 0.8. A preferred catalyst of this invention is of the formula

$RuNiCoZn_{0.4}$

The mixed metal oxide catalyst of this invention can be prepared in any one of a number of different methods. A typical and convenient method begins with dissolving in water a salt; e.g., a hydrated chloride, of each metal component of the catalyst and then adjusting the pH of the solution to above 7, typically above 8. The resulting slurry is then heated, filtered and washed thoroughly, dried, calcined and subsequently ground. The resulting catalytic composition can be used either in the 100% active form or in a diluted form; i.e., supported or unsupported. Suitable support materials include silica, titania, alumina, zirconia, silicon carbide, boron, various phosphates, etc. with low surface area (about 2 $m^2/g$) alumina a preferred support material. The support material can be incorporated into the catalyst along with the catalytic components or the catalytic composition can be coated and/or impregnated onto or into a support core. If a support is used, the catalytic composition is generally present in/on the support in an amount of at least about 1 wt. %, and up to about 30 wt % based on the combined weight of catalyst and support. Preferably, the catalysts used in this invention are supported.

Process Conditions

In the instant process there are two sequential hydrogenation stages. The hydrogenations may be carried out in the same or separate reactors. In a single reactor process, the process conditions at or near the reactor inlet are such that the maleic anhydride is cleanly converted to succinic anhydride, gamma-butyrolactone or mixtures thereof. The remainder of the reactor is maintained at process conditions for the conversion of the succinic anhydride and/or gamma-butyrolactone to 1,4-butanediol. In a two-reactor process, maleic anhydride is converted to succinic anhydride and/or gamma-butyrolactone in the first reactor and the succinic anhydride and/or gamma-butyrolactone rich effluent from the first reactor is passed directly into the second reactor for conversion to 1,4-butanediol.

The process of this invention can be conducted in either the liquid or gas phase or in a mixed liquid-gas phase. Process conditions may vary with the choice of catalyst.

The reaction temperature for the first stage is typically between about 100° and about 350° C. and preferably between about 150° and about 300° C. The first stage reaction pressure is between about 14.7 and 2500 psi. Preferably, the first stage reaction pressure is between 14.7 and 1500 psi. The $H_2$ to maleic anhydride ratio is between about 20/1 and about 600/1. The liquid hourly space velocity (LHSV) is between about 0.01/hr and about 10/hr and the hydrogen gas hourly space velocity (GHSV) is about 100/hr to about 100,000/hr.

The reaction temperature for the second stage is typically between about 180° and about 350° C. and preferably between about 200° and about 300° C. The reaction pressure is typically between about 200 and about 4000 psi and preferably between about 500 and 2000 psi. More preferred are pressures between about 750 and about 1500 psi.

Stoichiometric amounts of maleic anhydride and hydrogen are required for this process, but since hydrogen is both generally used in an undiluted form and is the principal source of pressure of the process, hydrogen is generally present in a large molar access. The amount of catalyst required to practice this invention can vary widely and is dependent upon a number of different factors, such as the starting hydrocarbon, hydrogen pressure, contact time, reactor size and design, etc. Typically, sufficient catalyst is packed into a fixed- or fluid-bed reactor and the reactants passed over and/or through a catalyst bed for continuous operation. In a batch operation, typically between about 0.1 and about 10 wt. %, and preferably between about 1 and about 5 wt. %, of active (without support) catalyst is used based upon the weight of the maleic anhydride.

As indicated in the preceding paragraph, the process of this invention can be practiced in virtually any kind of reactor that can accommodate the reaction conditions and accordingly, the contact time between the process reagents and catalyst will vary. In a continuous operation, such as a fixed- or fluid-bed reactor, typical contact times range from about 0.01 minutes to about 10 minutes. Contact times between about 0.1 minutes and 2 minutes are preferred. In a batch operation, the time will vary with the reaction starting materials, catalyst and conditions but a time between about 2 and 14 hours is usual.

This invention can be practiced either neat or in the presence of a solvent. Any solvent that will not prevent the hydrogenation of the process hydrocarbons can be used but solvents that are not extraneous to the process are preferred. For example water, dioxane, and $_1$-$C_4$ alkanols are suitable solvents but because they must be eventually removed from the reaction product, they are less desirable than gammabutyrolactone or tetrahydrofuran which will react to produce 1,4-butanediol and which are valuable by-products of the instant process. Products:

The invention provides high yields of 1,4-butanediol and minimizes the formation of undesirable brown tar-like products. Selectivity of the reactants to 1,4-butanediol greater than 90% are expected and selectivity greater than 95 are typical. The 1,4-butanediol is a commercial commodity and has a plurality of uses. For example, 1,4-butanediol is used in the production of polybutylene terephthalate and RIM urethanes.

This invention also produces small quantities of by-products, the most common being n-propanol and n-butanol These products are usually a result of the degradation of 1,4-butanediol and thus their amounts can be restrained by promptly removing the diol from the reaction product.

SPECIFIC EMBODIMENTS

The following examples are to be construed as merely illustrative, and not limitative of the remainder of the disclosure in any way whatsoever. The percent yields in all examples result from 100 percent conversion of the feed to the products and by-products.

EXAMPLE 1

Catalyst Preparation

The catalysts used in the following examples were mixed oxides coated on a 10–30 mesh alpha alumina support (surface area = 4 $m^2/g$), hereinafter referred to as "LSAA". In general the catalyst preparation involved impregnation of the LSAA to incipient wetness with a solution of Ni, Co, and Ru nitrates. After drying and calcination, the material was impregnated to incipient wetness with a zinc solution.

In a typical catalyst preparation, 220cc of LSAA was dried overnight in an oven as 120° C. 41.71g of a Ru(NO$_3$)$_3$ solution (8% Ru) was diluted with water to give a total weight of 88g and 9.59g of Co(NO$_3$)$_2$. 6H$_2$O and 9.59g of Ni(NO$_3$)$_3$.6H$_2$O were added. The alumina was impregnated with approximately half of the solution and dried at 120° C./4h. The remainder of the solution was impregnated onto the support which was then dried at 120° C./overnight and calcined at 350° C. for 3 hours. Half of the RuCoNi/LSAA was impregnated with a solution of 3.63g of Zn(OAc)$_2$.2H$_2$O in 22g of distilled water. The catalyst was dried at 120° C./overnight and calcined at 350° C. for 3h. This procedure resulted in a catalyst of the formula, Ru$_1$Co$_1$Ni$_1$Zn$_1$/LSAA.

EXAMPLE 2

Apparatus and Procedure

A high-pressure flow system was used in these experiments and included a 40cc fixed-bed reactor. The reactor was packed with 15 to 30 cc of catalyst. The remaining portion of the reactor was packed with glass beads. A liquid feed was pumped into the top of the reactor via a 1/16" stainless tubing.

Prior to testing, the catalyst was reduced at atmospheric pressure, in flowing H$_2$ (150sccm), at 300° C. The following temperature ramp was used in the reduction:

1. Rapidly to 100° C.
2. 100°–300° C. in 2h.
3. At 300° C. for 2 hr.
4. Cool to room temperature.

Following the reduction, the system was pressurized to 1300 psig and the hydrogen flow rate adjusted to between 1 and 6 SLM. The reactor and preheater were then heated to the desired temperatures (200°–250° C. and 120°–170° C., respectively). On reaching the set temperature, the liquid feed was introduced at about 6.5 cc/h. The product collection system was also cooled to ~0° C. The system was allowed to equilibrate for 5–24h prior to making the initial product collection. Typically a product collection lasted 2–3h, and during this time the effluent gas rate was measured. A sample of the effluent gas was taken at the midpoint of the collection for analysis.

EXAMPLE 3

A comparison between Maleic Anhydride (MAH)/Gammabutyrolactone (GBL) and Succinic Anhydride (SAH)/Gamma-butyrolactone (GBL) Hydrogenation Using catalysts prepared as described in Example 1 and the apparatus and procedure described in Example 2, the hydrogenation of two different feedstocks, MAH/GBL and SAH/GBL were compared. During the hydrogenation the reactor was operated at a pressure of 1300 psig, a temperature of 215° C., a hydrogen gas hourly space velocity (GHSV) of 8250/hr; a liquid hourly space velocity (LHSV) of 0.33/hr, and a contact time of 0.4 minutes. The data presented in Table 1 below was taken at approximately 25 hours of operation.

TABLE 1

A comparison between MAH/GBL and SAH/GBL Hydrogenation

|  | MAH/GBL | SAH/GBL |
| --- | --- | --- |
| Feed | 20% MAH in GBL | 17% SAH in GBL |
| Catalyst | RuCoNiZn$_{0.4}$/LSAA | RuCoNiZn/LSAA |
| % C$_4$ Conversion* | 13.4 | 22 |
| % Selectivity |  |  |
| 1,4-Butanediol | 82.1 | 92.9 |
| Tetrahydrofuran | 10.8 | 4.2 |
| Propanol | 2.0 | 2.1 |
| Butanol | 0.8 | 0.8 |
| CO$_2$ + CH$_4$ | 4.2 | ~0 |
| Mass Balance | 0.96 | 1.0 |

*% C$_4$ Conversion = $\frac{(S_{in} - S_{out})}{S_{in}} \times 100$ where S = (GBL + MAH + SAH)

The above test data illustrates that the overall conversion of SAH/GBL was twice that of MAH/GBL and the selectivity of the SAH/GBL to BDO was significantly greater than MAH/GBL to BDO. The above data further illustrates the desirability of a two-stage process for the hydrogenation of maleic anhydride to 1,4-butanediol where the first stage hydrogenates maleic anhydride to succinic anhydride and/or gamma-butyrolactone for further conversion to 1,4-butanediol.

The fact that slightly different catalyst compositions were employed in the test was believed to have only minimal or no effect on the activity variation since other similar testing with these catalysts has proven the two catalysts to have similar activities.

EXAMPLE 4

Hydrogenation of Neat gamma-butyrolactone (GBL)

Using catalyst (RuCoNiZn/LSAA) prepared as in Example 1 and the apparatus and procedure described in Example 2, GBL was hydrogenated. During the hydrogenation the reactor was operated at a set temperature of 200° C., pressure of 1300 psig, a hydrogen gas hourly space velocity (GHSV) or 2590/hr, a liquid hourly space velocity (LHSV) of 0.32/hr, and a hydrogen to hydrocarbon ratio of 27.

The results of the hydrogenation at approximately 50 hours are summarized in Table 2 below:

TABLE 2

Hydrogenation of Neat GBL Over RuCoNiZn/LSAA Catalyst

| % C$_4$ Conversion | 38.9 |
| --- | --- |
| % Selectivity to |  |
| 1,4-butanediol | 97.9 |
| Tetrahydrofuran | 1.1 |
| Propanol | 0.5 |
| Butanol | 0.3 |
| CH$_4$/CO$_2$ | 0.3 |
| Mass Balance | 0.93 |

The foregoing embodiments of the present invention have been presented for the purposes of illustration and description. This description is not intended to be exhaustive or to limit the invention to the precise form disclosed, and obviously many modifications and variations are possible in light of the above disclosure. The foregoing description attempts to best explain the principle of the invention and its practical applications and to thereby enable others skilled in the art to best utilize the invention in its various embodiments and with various modifications as are suited to the particular use contemplated. It is intended that the invention be defined by the following claims.

What is claimed is:

1. A process for the production of 1,4-butanediol comprising contacting at least one of maleic anhydride or maleic acid with hydrogen in a two stage process wherein in the first stage at least one of maleic anhydride or maleic acid is hydrogenated to at least one of succinic anhydride or gammabutyrolactone in the presence of a hydrogenation catalyst selected from the group consisting of copper chromite, copper chromite promoted with at least one additional metal or metal oxide, Pd/Al$_2$O$_3$, Pd on a carbon support, or a mixed oxide catalyst comprising copper, zinc and aluminum, and wherein in the second stage at least one of the succinic anhydride or gamma-butyrolactone is hydrogenated to 1,4-butanediol in the presence of a ruthenium-containing hydrogenation catalyst of the formula $$Ru_{0.001-2}M_{0.01-2}M'_{0.01-2}M''_{0.01-1}O_x$$

where

M is at least one of nickel and palladium,

M' is at least one of iron, cobalt, rhodium, osmium, iridium and platinum,

M" is at least one of zinc and cadmium, and x is a number sufficient to satisfy the valency requirements of the other elements present, and wherein the total contact time is about 0.1 minutes to 10.0 minutes.

2. The process of claim 1, wherein the temperature in the first stage is between about 100° C. and about 350° C.

3. The process of claim 1, wherein the temperature in the first stage is between about 150° C. and about 300° C.

4. The process of claim 1, wherein the temperature in the second stage is between about 150° C. and about 350° C.

5. The process of claim 1, wherein the temperature in the second stage is between about 200° C. and about 300° C.

6. The process of claim 1, wherein the pressure in the first stage is between about 14.7 and about 2500 psi.

7. The process of claim 1, wherein the pressure in the second stage is between about 500 and 2000 psi.

8. The process of claim 1, wherein the pressure in the second stage is between about 750 and 1500 psi.

9. The process of claim 1, wherein the liquid hourly space velocity is between about 0.01/hr and about 10/hr.

10. The process of claim 1, wherein the hydrogen gas hourly space velocity is about 100/hr to about 100,000 hr.

11. The process of claim 1, wherein at least one of maleic anhydride or maleic acid are dissolved in gamma-butyrolactone prior to the first hydrogenation stage.

12. The process of claim 1, wherein the ruthenium-containing catalyst is of the formula:

$$Ru_{0.01-2}M_{0.1-2}M'_{0.1-2}Zn_{0.3-0.5}O_x$$

where

M is at least one of nickel or palladium;

M' is at least one of iron cobalt and rhodium, and

X is a number sufficient to satisfy the valency requirements of the other elements present 13. The process of claim 1, wherein the catalyst is of the formula:

$$RuCo_{0.1-2}Ni_{0.1-2}Zn_{0.3-0.5}O_x$$

where X is a number sufficient to satisfy the valency requirements of the other elements present.

* * * * *